(12) United States Patent
Folkersen et al.

(10) Patent No.: US 8,906,613 B2
(45) Date of Patent: Dec. 9, 2014

(54) METHOD AND KIT FOR PERFORMING PROFILING OF ENDARTERECTOMY PATIENTS

(76) Inventors: Lasse Folkersen, Stockholm (SE); Anders Gabrielsen, Bromma (SE); Ulf Hedin, Ronningen (SE); Gabrielle Paulsson-Berne, Bromma (SE); Jonas Lars Persson, Stockholm (SE)

( * ) Notice: Subject to any disclaimer, the term of this patent is extended or adjusted under 35 U.S.C. 154(b) by 193 days.

(21) Appl. No.: 13/396,055

(22) Filed: Feb. 14, 2012

(65) Prior Publication Data

US 2013/0210636 A1 Aug. 15, 2013

(51) Int. Cl.
*C12Q 1/68* (2006.01)
(52) U.S. Cl.
USPC .............................. 435/6.1; 600/301; 600/483
(58) Field of Classification Search
None
See application file for complete search history.

(56) References Cited

U.S. PATENT DOCUMENTS 6,524,795 B1 * 2/2003 Francis et al. ............... 435/6.16
7,794,413 B2 * 9/2010 Soito et al. ................... 600/587

* cited by examiner

*Primary Examiner* — Jim Ketter
(74) *Attorney, Agent, or Firm* — Ziegler IP Law Group, LLC

(57) ABSTRACT

A method of profiling endarterectomy patients for determining one or more post-operative risks includes steps comprising:
  (a) obtaining a set of parameters which describe the patient, the set of parameters including at least one of: age of patient, E; smoking habits of patient, S; serum cholesterol concentration of patient, C; diabetes status of patient, D; blood pressure of patient, P;
  (b) obtaining one or more samples of plaque tissue from endarterectomy treatment of the patient;
  (c) isolating genetic material from the one or more samples of plaque tissue;
  (d) determining genetic expression activities of a plurality of genes identified in the genetic material; and
  (e) computing from the set of parameters in combination with the genetic expression activities one or more post-operative risks indicative of potential events to which the patient is susceptible as a consequence of the endarterectomy treatment.

20 Claims, 2 Drawing Sheets

METHOD AND KIT FOR PERFORMING PROFILING OF ENDARTERECTOMY PATIENTS

FIELD OF THE INVENTION

Figure 1:
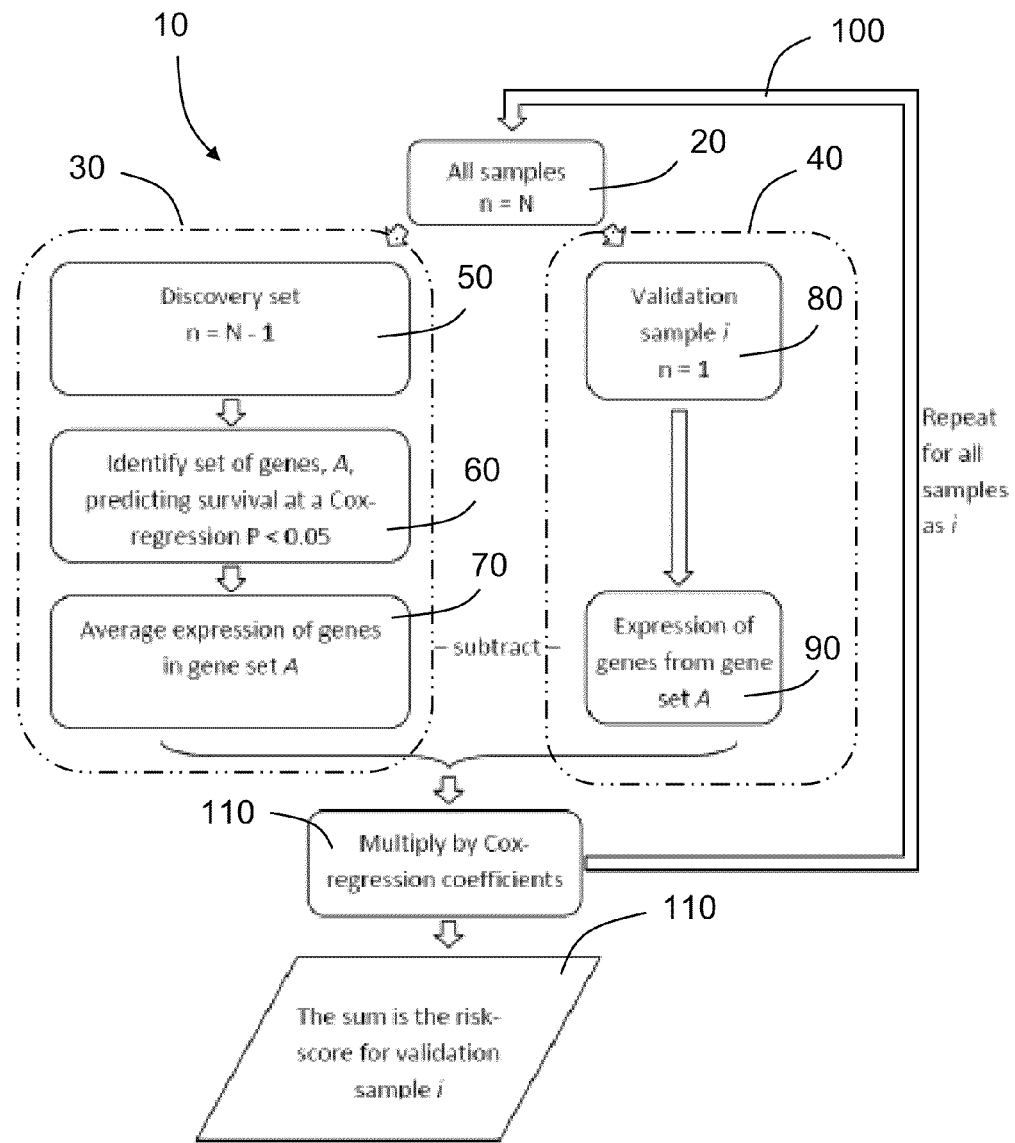

The present invention concerns methods of profiling endarterectomy patients, for example for determining risk factors and associated optimal post-operative treatment strategies. Moreover, the present invention also relates to kits for use for executing such methods. Furthermore, the invention concerns software products recorded on machine-readable data storage media, wherein the software products are executable on computing hardware for assisting in executing aforesaid methods.

BACKGROUND OF THE INVENTION

"Endarterectomy" refers to a removal of material from an inside surface of the one or more arteries; the material on the inside surface is known as "plaque" and is often mechanically of a sticky flexible nature. An example of an endarterectomy procedure is Carotid endarterectomy (CEA), which is a surgical procedure employed to reduce a risk of stroke by at least partially correcting for stenosis, namely narrowing, in one or more common carotid arteries of the human body.

A natural process known as Atherosclerosis which occurs in the human body causes layers of plaque to form in the one or more arteries. In the carotid arteries atherosclerosis usually occurs in a fork where a common carotid artery divides into a corresponding internal carotid artery and a corresponding external carotid artery. The layers of plaque have a tendency to build up in the inner surfaces of the arteries, namely lumen, and cause narrowing and associated constriction of the arteries, thereby rendering blood supply to the human brain at least partially restricted. Pieces of the plaque, known as emboli, are susceptible to break off, namely become embolized, and travel up the internal carotid artery to brain regions, whereat the pieces risk blocking blood circulation, and thereby risk causing death of brain tissue which requires to be constantly furnished with oxygen and nutrients to survive.

In practice, it is found that the layers of plaque cause symptoms which are noticeable by patients themselves. The symptoms are often experienced as temporary or transitory strokes, namely transient ischemic attacks (TIA's). For purposes of conventional temporary diagnosis, TIA's last less than 24 hours; after 24 hours, TIA's are known as strokes.

In situations where the plaque does not manifest as noticeable symptoms, patients are still at a higher risk of stroke in comparison to a general human population, but not as high a risk for patients with symptomatic stenosis. An incident of stroke, including fatal stroke, is in a range of 1% to 2% per year. Surgical mortality as a result of executing endarterectomy lies often in a range of 1% to 2% of patients, but is susceptible to lying in a larger range of 1% to 10% in certain circumstances. Thus, execution of endarterectomy potentially provides potential benefits but also introduces additional risk.

In carotid endarterectomy, a surgeon opens a human carotid artery of a patient to be treated and mechanically removes plaque, namely a sticky fat-like material from the artery. A newer procedure, known as endovascular angioplasty, threads a catheter up from a groin region of the patient, around an aortic arch, and up a carotid artery to be de-plagued. The catheter employs a balloon-type structure to expand the artery, thereby providing an opportunity for a stent to be fitted to hold the artery open if required. In a plurality of clinical trials, a 30-day post-operative risk of heart attack, stroke, or even death was significantly higher when stenting was employed in comparison to just endarterectomy, namely 9.6% for stenting versus 3.9% for endarterectomy. The European International Carotid Stenting Study (ICSS) found that stents had almost double a rate of complications occurring in comparison to just endarterectomy.

When performing endarterectomy on patients, it is desirable to try to reduce a risk of post-operative complications, for example post-operative complications which can result in strokes, or worst case death, and also short- and longterm progression of atherosclerosis. Contemporary risk prediction methods for use in selecting appropriate post-operative treatments for endarterectomy patients involves assessing parameters indicative of:

(a) age of patient, E;
(b) smoking habits of patient, S;
(c) serum cholesterol concentration of patient, C;
(d) diabetes status of patient, D; and
(e) blood pressure of patient, P.

The risk prediction determines a degree of aftercare required, for example prescribed certain types of medication, or subjected to additional invasive treatments; the risk R and a suitable treatment strategy T are defined by Equations 1 and 2 (Eq. 1, Eq. 2):

$$R = F_1(E,S,C,D,P) \qquad \text{Eq. 1}$$

$$T = F_2(E,S,C,D,P) \qquad \text{Eq. 2}$$

wherein $F_1$ and $F_2$ are multi-parameter functions.

A problem arising in practice is that Equations 1 and 2 (Eq. 1 & Eq. 2) are not sufficiently accurate, such that individuals susceptible to short-term and long term major cerebrovascular and cardiovascular ischemic events are not identified accurately. A more accurate risk prediction is desirable which will aid medical staff to treat high-risk patients more aggressively than others.

SUMMARY OF THE INVENTION

The present invention seeks to provide an improved method of performing profiling of one or more endarterectomy patients for reducing a risk of complications or mortality after endarterectomy treatment has been executed on the one or more patients.

Moreover, the present invention seeks to provide testing kits including necessary elements for implementing the improved method of performing profiling of one or more endarterectomy patients for reducing a risk of complications or mortality after endarterectomy treatment has been executed on the one or more patients.

According to a first aspect of the present invention, there is provided a method as defined in appended claim 1: there is provided a method of profiling endarterectomy patients for determining one or more post-operative risks, characterized in that the method includes:

(a) obtaining a set of parameters which describe the patient, the set of parameters including at least one of: age of patient, E; smoking habits of patient, S; serum cholesterol concentration of patient, C; diabetes status of patient, D; blood pressure of patient, P;
(b) obtaining one or more samples of plaque tissue from endarterectomy treatment of the patient;
(c) isolating genetic material from the one or more samples of plaque tissue;
(d) determining genetic expression activities of a plurality of genes identified in the genetic material; and
(e) computing from the set of parameters in combination with the genetic expression activities one or more post-operative risks indicative of potential events to which the patient is susceptible as a consequence of the endarterectomy treatment.

The present invention is of advantage in that the method is capable of providing better prediction of one or more risks of ischemic events than conventional methods after endarterectomy treatment.

Optionally, the method is used for carotid endarterectomy and the method includes obtaining one or more samples of plaque tissue from carotid endarterectomy treatment of the patient.

Optionally, the method is implemented, so that the isolated genetic material corresponds to a total RNA content of the one or more samples of plaque tissue. Plaque tissue is of advantage because it is capable of providing a better indication of the one or more risk factors used for prediction of ischemic events in comparison to genetic material obtained from blood cells.

Optionally, the method is implemented, so that a step (e) of the method includes excluding from computation of the one or more risks gene expressions which lie below a threshold expression limit. Such a limit prevents irrelevant genes from influencing the assessment of the one or more risks. More optionally, the threshold expression limit is determined from an average expression exhibited by a plurality of genes obtained from the one or more samples of plaque tissue.

Optionally, the method includes excluding from computation of the one or more risk factors RNA material from one or more genes whose RNA purity is less than a purity threshold limit. Such a filtration prevents extraneous material from influencing computations of the one or more risks.

Optionally, the method in its step (e) involves performing a blinded cross-validation iterative computation for computing the one or more risks.

Optionally, for obtaining most pertinent material for analysis, the plurality of genes are derived from cytoplasm, plasma membranes and mitochondria included in the one or more samples of plaque tissue. More optionally, the genetic material includes a set of genes, wherein substantially 13.2% of the genes are localized to cytoplasm.

Optionally, substantially 14.9% of the genetic material is localized to plasma membranes, and substantially 3.5% of the genetic material is localized to mitochondria.

Optionally, the method includes in its step (e) of the method involves computing Cox regression coefficients for assigning a gene expression-based risk score to the patient.

Optionally, the method includes an additional step of designing a post-treatment care strategy based upon the computed one or more post-operative risk factors indicative of potential events.

According to a second aspect of the invention, there is provided a kit for use to implement a method pursuant to the first aspect of the invention.

According to a third aspect of the invention, there is provided a software product stored machine-readable data media, the software product being executable upon computing hardware for implementing a method pursuant to the first aspect of the invention.

It will be appreciated that features of the invention are susceptible to being combined in any combination without departing from the scope of the invention as defined by the appended claims.

DESCRIPTION OF THE DIAGRAMS

Figure 2:
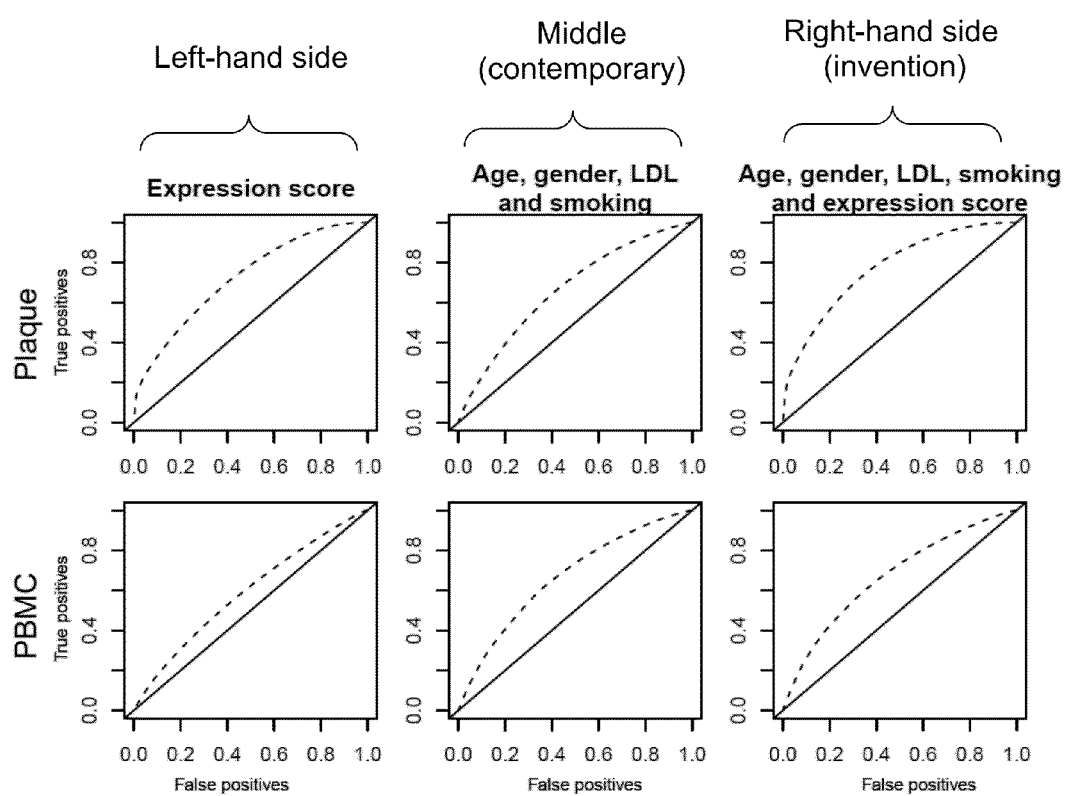

Embodiments of the present invention will now be described, by way of example only, with reference to the following diagrams wherein:

FIG. 1 is an illustration of an algorithm for use when implementing the present invention; and FIG. 2 is a set of graphs illustrating effectiveness of the algorithm of FIG. 1.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS OF THE INVENTION

It is potentially of considerable clinical interest to identify which patients have an excess risk of future events, e.g. in cardiovascular events, because it provides a first step in applying intensified preventative measures to assist the patients at excess risk to survive; it is thus an issue of life or death. Contemporarily considered risk factors, such as age, gender, smoking habits, diabetes status, hypercholesterolemia and hypertension are well documented and easily identifiable in practice by conducting simple tests on patients. However, it is desirable to improve associated method of assessing post-operative risk. The present invention is distinguished in that its methods involve obtaining, alternatively or additionally to aforementioned parameters of Equations 1 and 2 (Eq. 1 & Eq. 2), genotype and gene expression profiles from plaque material extracted during carotid endarterectomy. Optionally, blood samples obtained during carotid endarterectomy providing mononuclear cells are also subjected to genotype and gene expression profiling to provide additional information for guiding post-endarterectomy care of patients. However, as will be elucidated in further detail later, genetic analysis of multiple genes in plaque tissue provides most reliable indications of post-operative risk.

The methods of the present invention have been evolved from a sample of 126 patients who have undergone plaque tissue removal during carotid endarterectomy treatment, and 97 patients whose mononuclear blood cells were collected during endarterectomy treatment. The patients were followed for an average of 44 months during which 25 major adverse cardiovascular, cerebrovascular or vascular events (i.e. 18 ischemic strokes and 7 myocardial infarctions) were registered. Blinded "leave-one-out" cross-validation on Cox regression coefficients was used to assign a gene expression-based risk score to each patient in the study. It should be noted that the method of "leave-one-out" cross-validation is one of several methods which could be used to determine the risk factors. The person skilled in the art will be aware of other methods than "leave-one-out" cross-validation useful to perform the analysis as proposed in the following embodiments. When compared to risk factors computed using contemporary known methods, the method of the invention is capable of predicting future adverse post-operative events from an area-under-curve (AUC) basis by at least from 0.66 to 0.79, namely an improvement of 0.13 AUC units. It was found that information obtained from the carotid plaque was most reliable for improving accuracy of prediction of the risk. Better assessment of risk thus has an important benefit of potentially reducing patient mortality or injury through an improved treatment strategy for patients.

Methods of the invention will now be described in greater detail. The present invention was devised using materials supplied from the Karolinska Carotid Endarterectomy Biobank (BiKE) after all patients provided informed written consent, pursuant to the Declaration of Helsinki and the Karolinska Institute Ethics Committee (journal no. 02-147 and 2009/295-31/2). The study included 97 peripheral blood mononuclear cell (PBMC) samples and 126 atherosclerotic plaque tissue samples from Caucasian patients who were undergoing carotid endarterectomy at Karolinska University Hospital, Sweden. The PBMC and plaque samples had 97 common overlapping samples; in other words, the PBMC samples represented a subset of the plaque samples. An overview of the samples is provided in Tables 1 and 2:

TABLE 1

Baseline characteristics of data sets

| | Microarray | |
|---|---|---|
| | Plaque | PBMC |
| N | 126 | 97 |
| Follow-up time (days) | 1333 +/− 728 | 1159 +/− 631 |
| Age (years) | 70.6 +/− 8.9 | 70.8 +/− 9.38 |
| Body mass index (kg/m$^3$) | 26.4 +/− 3.8 | 26.5 +/− 4.15 |
| Low density lipoprotein (mmol/l) | 2.52 +/− 0.94 | 2.46 +/− 0.97 |
| Ischemic Events during follow up | 19.8% (25) | 21.6% (21) |
| Female gender | 22.2% (28) | 25.8% (25) |
| Current or previous smoker | 49.2% (62) | 49.5% (48) |
| Type 2 Diabetes status | 25.4% (32) | 26.8% (26) |
| Symptomatic carotid artery disease | 67.5% +/− (85) | 69.1% +/− (67) |

TABLE 2

Genotype scores for samples employed to develop the present invention

| | Model | AUC |
|---|---|---|
| Plaque data set (N = 126) | Genotype score only | 0.55 |
| | Expression score only | 0.72 |
| | Classical risk markers | 0.66 |
| | Combination | 0.79 |
| PBMC data set (N = 97) | Genotype score only | 0.55 |
| | Expression core only | 0.59 |
| | Classical risk markers | 0.67 |
| | Combination | 0.68 |

Table 2 provides an indication of an "area under the curve" (AUC) at 300 days after a carotid endarterectomy operation being executed on the patients. The genotype score is based on a risk allele count in 25 previously published myocardial infarction associated risk variants. The expression score is based on mRNA expression levels of a set of predictive genes associated with the studied plaque tissue. Classic risk scores in Table 2 are based upon known contemporary methods, namely are based upon a parameters indicative of age, gender, serum low-density lipoproteins (LDL) and smoking status. The combination score corresponds to an inclusion of all parameters in a multivariate model employed in methods pursuant to the present invention.

Methods pursuant to the present invention include a step of isolating total RNA from plaque samples and/or blood cell samples, for example by using a proprietary RNeasy Mini Kit manufactured by Qiagen; "RNeasy" is a trade mark of Qiagen. The isolated total RNA is then treated using a RNase-free DNase kit, also manufactured by Qiagen; "RNase" is a trade mark of Qiagen. A RNA sample thereby obtained is, pursuant to the present invention, then in a subsequent step analyzed for quality, for example using a proprietary Agilent 2100 bioanalyzer manufactured by Agilent Technologies Inc., Palo Alto, Calif.; RNA concentration pursuant to a step of the method is measured, for example using a NanoDrop apparatus manufactured by a company Thermo Scientific. The method thereby defines a threshold for RNA quality, such that RNA material not satisfying threshold criteria of quality is not used for determining risk and treatment strategies pursuant to the present invention. Such quality filtering is beneficially for improving reliability of methods pursuant to the present invention.

RNA samples pursuant to the present invention are thereafter hybridized and then scanned to determine their characteristics, for example at the Karolinska Institute Affymetrix core facility using Affymetrix HG-U133 plus 2.0 arrays. Resulting cel data files generated from such scanning, namely data collected from the arrays, are then processed, for using Robust Multichip Average (RMA) normalization, for example data processing functionality provided by execution of Affymetrix Power Tools 1.10.2 software on computing hardware, Beneficially, RMA normalization is performed using official Affymetrix chip definition files (CDFs) or custom CDF files. In the custom CDF file, a probe set corresponds to a gene, whereas in a standard CDF, there are 2.1 probe sets per gene. Beneficially, the custom CDF file is downloaded as a version 13.0.0 of HGU133Plus2_Hs_ENTREZG. As a part of RMA normalization, all expression measurements were log 2-transformed. Low-expression probe sets whose average expression levels are less than a genome-wide median value for expression levels are omitted from analysis executed as a step of the method of the present invention; the measurements are thus subjected to an expression filter subject to a lower acceptable expression threshold, wherein the threshold is based upon a median expression exhibited by the genes in the sample.

The method of the invention involves a step of genotyping, wherein DNA samples, for example from the aforementioned BiKE patients, for example using proprietary Illumina Human 610W-Quad Beadarrays available at the SNP technology platform at Uppsala University. Beneficially, the method makes use of proprietary GenomeStudio (trade mark, TM) software purchasable from Illumina for use in genotype calling and quality control. When executing the method, it is practical to expect an average call rate per SNP of 99.84%. For example, the inventor found during development of the present invention that replication genotyping of 12 samples demonstrated an overall concordance of 99.99%. Of 29 SNPs, it was found that only 25 SNPs could be imputed to be of a satisfactory quality for use in determining proposed treatment strategy results from the method, namely Rsq-score>0.3, using a proprietary MACH algorithm. These SNPs investigated were rs10953541, rs11206510, rs1122608, rs11556924, rs12190287, rs12526453, rs12936587, rs1412444, rs17114036, rs17228212, rs1746048, rs17465637, rs17609940, rs216172, rs2505083, rs2943634, rs4380028, rs46522, rs4977574, rs579459, rs646776, rs6725887, rs6922269, rs964184, and rs974819 which had been found by other research groups.

Beneficially, the method involves comparing allele frequencies of risk SNPs with measured allele frequencies to ensure a more correct choice of risk allele. An overall genotype risk score is, pursuant to the method, computed as a sum of risk alleles for each patient. Further from the analysis performed it was seen that SNPs associated with early myocardial infarction add some predictive value through additional information on the risk of ischemic events in patients.

The method pursuant to the present invention beneficially employs a complete "leave-out-one" cross validation. For each iteration, all sample results from RNA analysis except a result from one analysis are used to select probe sets whose expression levels are predictive of future post-operative events. For each probe set, the cross validation is beneficially achieved using Cox regression calculation software. All probe sets preferably have a Cox regression significance of P<0.05 for predicting a risk score for the omitted sample. The risk score for the omitted sample is defined by Equation 3 (Eq. 3):

$$risk_i = \sum_{j \in A}^{j} coefficient_j \times (expression_{ji} - expression_j) \quad \text{Eq. 3}$$

wherein
j=index identifying a probe set;
A=a group of probe sets, for example with a Cox regression significance P<0.05;
coefficient=is a Cox coefficient of a probe set; and
expression$_{ji}$=is the probe set expression in the omitted sample; and
expression$_j$=is a mean expression of the probe set in the remaining samples.

The cross validation as an iterative procedure using Equation 3 (Eq. 3) is repeated until all samples have been assigned a risk score, based on gene selection and gene expression weights, namely selected independently of the expression profile in the sample. FIG. 1 illustrates steps of this analysis process beneficially used in the method of the invention.

Contemporary known risk markers, namely cross-validated gene expression risk scores, and the risk allele counts of genotypes are beneficially used as variables in the method of the present invention, for example as included in aforesaid Table 2. The proportional hazards assumption holds globally for all variables in both plaque and PBMC data sets. However, for specific variables, smoking may potentially violate the assumptions, generating a decreasing time-dependent effect. Pursuant to the present method, ROC curves are plotted, and areas under the curve (AUC) are calculated using, for example, a riskset ROC R-package software product.

The method of the invention may in an embodiment also utilize a characteristic of a gene expression profile that comprises multiple genes rather than a single gene expression is a more robust predictor of survivability, namely a risk indicator, for post-operative problems associated with carotid endarterectomy. E.g. a contemporary micro-array discovery in such an embodiment could be followed by, or replaced by, real-time PCR validation schemes used for determining individual gene expressions, the present invention would be concerned with methods of determining gene-wide expression associated with a multiplicity of genes, hence prompting adoption, for example, of leave-one-out cross-validation schemes as aforementioned.

In FIG. 1, steps of an algorithm are indicated generally by 10. The algorithm 10 includes a first step 20 of analyzing all samples, namely as aforementioned in respect of their total RNA content. Thereafter, from step 20, there are two parallel branches 30, 40. A first branch 30 includes a leave-one-out subset in a step 50 for providing a discovery set of samples. After the step 50 in the branch 30, a subsequent step 60 is concerned with identifying a set of genes A which are predicting survival at a Cox regression below a given threshold, for example a Cox regression factor P<0.05. After the step 60, the branch 30 includes a step 70 for computing an average expression of genes present in the gene set A. In the parallel branch 40, a step 80 is concerned with generating a validation sample i, wherein n=1. In a step 90 after the step 80 in the parallel branch 40, the step 90 is concerned with determining the expression of genes from the set A for n=1.

From the steps 70, 90 an iteration step 100 is implemented for computing multiplications by Cox-regression coefficients until all samples are considered for i. At a final step 120, a sum corresponding to a risk score for the validation sample i is computed. The computed risk score is then used for determining a most appropriate post-treatment care strategy for reducing a likelihood of post-treatment events which could potentially cause patient injury or even death. The R-code for the scheme shown in FIG. 1 can be found in the Appendix as supplementary S3.

When implementing the algorithm in respect of samples obtained from the Karolinska University Hospital (BiKE), plaque gene expression profiles determined from a plurality of genes result in a risk score which differs significantly between patients with post-operative events after carotid endarterectomy, and those patients without such events. Thus, the method of the present invention is operable to identify patients potentially at risk of post-operative complications so that additional care activities can be undertaken to assist such patients at risk, for example in respect of administration of medication, retention in hospital facilities and so forth.

In FIG. 2, there is shown a series of graphs illustrating characteristic curves for different risk factors at 300 days post-operative to executing endarterectomy treatment. The analysis was also performed at 10 and 100 days, which results showed similar results to that seen at 300 days. Top plots, namely "expression score", "age, gender, LDL and smoking", "age, gender, LDL, smoking and expression score", in FIG. 2 illustrate data from a plaque tissue data set. Bottom plots, namely from a "PBMC" data set, pertain correspondingly to peripheral blood monoculture cells data set. The plots are computed only from gene expression profiles (left), only for established risk factors including age, gender, LDL and smoking (left and middle), or from gene expression profiles and the four established risk factors (right). A straight diagonal line in each graph indicates a prediction from pure chance, wherein AUC=0.5. The curved lines in FIG. 2 denote a prediction which is possible with the predictive variables. For comparison, a curve following an upper left-hand periphery of the graphs would represent an excellent prediction of highly relevant post-treatment risk factor. It will be seen from FIG. 2 right-hand-side graphs that the present invention is capable of providing an improvement in prediction, particularly when gene analysis from collected plaque is employed, but potentially may not be capable of making a perfect prediction of risk. However, even a moderate increase in predictive performance can save patient lives.

FIG. 2 illustrates predictive power of three models: risk expression score only (left), contemporary risk factor profiling (middle), and a combination of conventional risk factor profiling and gene expression risk score (right). The right-hand-side graphs in FIG. 2 are illustrative of a method pursuant to the present invention. As illustrated in FIG. 2, plaque expression profiling predicts post-operative events more accurately than PBMC expression profiling. Thus, by using gene expression risk profiling in combination with contemporary known risk marker prediction, it is feasible to improve risk prediction of post-operative events occurring and is thereby capable of ensuring more appropriate treatment strategies based on the risk of post-operative events occurring.

The cross-validation risk-prediction score demonstrates the general utility of gene expression profile-based prediction. On account of cross-validation beneficially employed when implementing the present invention, the actual list of probe sets employed for profiling depends on the sample that is omitted. When developing practical embodiments of the present invention, on average, 192+/−38 probe sets were used to profile each leave-one-out iteration, see FIG. 1 for the iteration. The leave-one-out iteration approach was used to validate the method of the profiling of the plaque for prediction and can further be used to optimize different practical embodiments of the present invention depending on application. Moreover, 18.3% of the probe sets were present in more than 90% of the iterations, and 66.2% of the probe sets were present in less than 10% of the iterations. The 146 probe sets that were presented in more than 90% of the iterations are shown in Supplementary S1 in the Appendix pg. 18-19.

Tests made during development of the present invention identified that there are 146 genes which are best predictors of future post operative events after carotid endarterectomy has been implemented; optionally, the present invention involves the assessment of at least 100 most suitable genes. Of the genes quantities thereof were in the ranges of 10 to 30% range, more preferably in the range of 10 to 20% and most preferably substantially 13.2% are localized to cytoplasm, a range of 10 to 20%, more preferably in the range of 13% to 17% and most preferably substantially 14.9% are localized to plasma membranes, a range of 4 to 10%, more preferably in the range of 2% to 5%, and most preferably substantially 3.51% are localized to mitochondria, a range of 9% to 12.5% and more preferably substantially 11.4% are localized in the nucleus according to a cellular compartment library provided by Gene Ontology. This result clearly indicates that algorithms based upon characterization of individual gene expressions will not yield as reliable results as provided by the present invention which takes into consideration expression of a set of mutually different genes, most beneficially derived from plaque samples obtained when performing carotid endarterectomy.

According to the present invention, a method of using gene expression profiles from carotid endarterectomy samples is capable of providing an improved risk projection of future post-operative events. Such events have implications for clinical care required for patients, for example for identifying high risk patients who need an enhanced degree of care, for example aggressive risk factor interventions. For very high risk patients identified using the method of the present invention, there is an indication of advanced progress-rate of atherosclerosis and an individualized tailored pharmacological treatment is beneficially employed to avoid occurrence of secondary ischemic events. Such tailored treatment can include one or more of: medication for blood pressure regulation, blood thinning agents, cholesterol controlling medications (for example lipid lowering therapy), barometric treatment, exercise regimes (for example weight control), optimal diabetes treatment, smoking cessation and so forth. Further to the treatment, patients with higher risk factors than others beneficially return back to the physician/ambulatory clinic regularly, for example once every second week instead of once every second month as is often the case today. However, these patients might have to tolerate more side-effects of the medication and so forth.

According to methods pursuant to the present invention present invention, it is highly beneficial to use several genes in a combination profile, rather than focusing on individual genes. Plaque tissue dissected during a carotid endarterectomy treatment provides much better expression-based prediction of post-treatment events than predictable from circulating blood cells. When verifying benefits provided by methods of the invention, results were based on gene expression profiles in 126 patients who experienced 25 ischemic events. All gene selections and risk score calculations are beneficially performed in a blinded cross-validation iteration and therefore constitute a single risk score variable in prediction computations as illustrated in FIG. 2.

The present invention also concerns a kit for performing methods pursuant to the invention. The kit includes apparatus necessary for analyzing plaque tissue, for measuring gene expression of a plurality of genes present in the plaque sample and generating corresponding measurement data, and computer software products executable on computing hardware for receiving the measurement data, processing the data and providing an overall assessment of risk factor associated with post-operative events after carotid endarterectomy treatment. Optionally, the risk factor is linked to a computer-based expert system which proposes a preferred course of post-operative care which reduces a risk of patient degradation or mortality. The kit optionally includes one or more items of contemporary proprietary apparatus described in the foregoing or equivalently functional apparatus.

Modifications to embodiments of the invention described in the foregoing are possible without departing from the scope of the invention as defined by the accompanying claims. For example, the present invention is beneficially used for the profiling of all arteries in case of surgery/endarterectomy. Further plaques obtained from vascular surgery/endarterectomy surgery on e.g. iliaca arteries, femoral arteries, coronary arteries and/or internal mammary arteries would also benefit from the embodiments described. In vascular surgery of peripheral arteries, coronary arteries, carotid arteries and the genetic profile of each and every sample obtained provides information about atherosclerosis progress. This provides one or more risk factors from arteries retrieved through surgery and providing valuable information on the progress-rate of atherosclerosis.

Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

APPENDIX

Example of Analysis

Prediction of Ischemic Events Based on Transcriptomic and Genomic Profiling in Patients Undergoing Carotid Endarterectomy S1) Predictive Genes from Standard CDF Probe sets that were present in more than 90% of the leave-one-out iterations. This expression signature represents the genes with the best predictive properties in this data set. Pg. 18-19

S2) Predictive Genes from Custom CDF

Probe sets that were present in more than 90% of the leave-one-out iterations when using alternative annotation from custom CDF files as described in the main text. The purpose of this investigation was to ensure that predictive power did not arise from annotation artifacts. Pg. 20

S3) R-Code for Calculating Expression Risk Scores

Given a bioconductor ExpressionSet and a text file with survival data, this script will calculate the expression risk score as described in the main text. The purpose of including this script is to give the complete details of the steps taken in the cross-validation procedure. Pg. 21-24

S1

| Standard CDF probe set ID | genesymbol | Genename | number of leave-one-out iterations |
|---|---|---|---|
| 201511_at | AAMP | angio-associated, migratory cell protein | 124 |
| 227324_at | ADCK4 | aarF domain containing kinase 4 | 118 |
| 223183_at | AGPAT3 | 1-acylglycerol-3-phosphate O-acyltransferase 3 | 122 |
| 222228_s_at | ALKBH4 | alkB, alkylation repair homolog 4 (*E. coli*) | 121 |
| 39248_at | AQP3 | aquaporin 3 (Gill blood group) | 126 |
| 219636_s_at | ARMC9 | armadillo repeat containing 9 | 118 |
| 206129_s_at | ARSB | arylsulfatase B | 117 |
| 212069_s_at | BAT2L | HLA-B associated transcript 2-like | 126 |
| 221320_at | BCL2L10 | BCL2-like 10 (apoptosis facilitator) | 123 |
| 244738_at | BRWD3 | bromodomain and WD repeat domain containing 3 | 122 |
| 207485_x_at | BTN3A1 | butyrophilin, subfamily 3, member A1 | 126 |
| 209846_s_at | BTN3A2 | butyrophilin, subfamily 3, member A2 | 126 |
| 229801_at | C10orf47 | chromosome 10 open reading frame 47 | 123 |
| 219435_at | C17orf68 | chromosome 17 open reading frame 68 | 122 |
| 237131_at | C1orf230 | chromosome 1 open reading frame 230 | 123 |
| 231360_at | C20orf141 | chromosome 20 open reading frame 141 | 121 |
| 235181_at | C2orf60 | chromosome 2 open reading frame 60 | 124 |
| 225559_at | C3orf19 | chromosome 3 open reading frame 19 | 124 |
| 236296_x_at | C8orf58 | chromosome 8 open reading frame 58 | 121 |
| 223495_at | CCDC8 | coiled-coil domain containing 8 | 122 |
| 219025_at | CD248 | CD248 molecule, endosialin | 120 |
| 234008_s_at | CES3 | carboxylesterase 3 | 124 |
| 225690_at | CRKRS | Cdc2-related kinase, arginine/serine-rich | 126 |
| 206974_at | CXCR6 | chemokine (C-X-C motif) receptor 6 | 126 |
| 214788_x_at | DDN | Dendrin | 125 |
| 219811_at | DGCR8 | DiGeorge syndrome critical region gene 8 | 120 |
| 232434_at | DIRC3 | disrupted in renal carcinoma 3 | 124 |
| 202571_s_at | DLGAP4 | discs, large (*Drosophila*) homolog-associated protein 4 | 124 |
| 211624_s_at | DRD2 | dopamine receptor D2 | 116 |
| 224966_at | DUS3L | dihydrouridine synthase 3-like (*S. cerevisiae*) | 120 |
| 1557480_a_at | DYSFIP1 | dysferlin interacting protein 1 | 118 |
| 210132_at | EFNA3 | ephrin-A3 | 125 |
| 223682_s_at | EIF1AD | eukaryotic translation initiation factor 1A domain containing | 120 |
| 208725_at | EIF2S2 | eukaryotic translation initiation factor 2, subunit 2 beta, 38 kDa | 126 |
| 201123_s_at | EIF5A | eukaryotic translation initiation factor 5A | 126 |
| 219436_s_at | EMCN | Endomucin | 116 |
| 201313_at | ENO2 | enolase 2 (gamma, neuronal) | 120 |
| 219759_at | ERAP2 | endoplasmic reticulum aminopeptidase 2 | 126 |
| 213468_at | ERCC2 | excision repair cross-complementing rodent repair deficiency, complementation | 125 |
| 227203_at | FBXL17 | F-box and leucine-rich repeat protein 17 | 126 |
| 211734_s_at | FCER1A | Fc fragment of IgE, high affinity I, receptor for; alpha polypeptide | 118 |
| 235250_at | FLCN | Folliculin | 125 |
| 231882_at | FLJ39632 | hypothetical LOC642477 | 117 |
| 204948_s_at | FST | Follistatin | 126 |
| 201635_s_at | FXR1 | fragile X mental retardation, autosomal homolog 1 | 123 |
| 201723_s_at | GALNT1 | GalNAc-T1 | 121 |
| 223487_x_at | GNB4 | guanine nucleotide binding protein (G protein), beta polypeptide 4 | 119 |
| 208965_s_at | IFI16 | interferon, gamma-inducible protein 16 | 122 |
| 230172_at | IFI27L1 | interferon, alpha-inducible protein 27-like 1 | 121 |
| 224079_at | IL17C | interleukin 17C | 125 |
| 205798_at | IL7R | interleukin 7 receptor | 117 |
| 1557080_s_at | ITGBL1 | integrin, beta-like 1 (with EGF-like repeat domains) | 117 |
| 202747_s_at | ITM2A | integral membrane protein 2A | 126 |
| 202182_at | KAT2A | K(lysine) acetyltransferase 2A | 119 |
| 211217_s_at | KCNQ1 | potassium voltage-gated channel, KQT-like subfamily, member 1 | 116 |
| 214471_x_at | LHB | luteinizing hormone beta polypeptide | 121 |
| 212935_at | MCF2L | MCF.2 cell line derived transforming sequence-like | 120 |
| 213696_s_at | MED8 | mediator complex subunit 8 | 121 |
| 214269_at | MFSD7 | major facilitator superfamily domain containing 7 | 126 |
| 231255_at | MPRIP | myosin phosphatase Rho interacting protein | 125 |
| 218678_at | NES | Nestin | 115 |
| 238530_at | NNT | nicotinamide nucleotide transhydrogenase | 122 |
| 211143_x_at | NR4A1 | nuclear receptor subfamily 4, group A, member 1 | 126 |
| 209959_at | NR4A3 | nuclear receptor subfamily 4, group A, member 3 | 126 |
| 233795_at | ODF3 | outer dense fiber of sperm tails 3 | 117 |
| 224745_x_at | OTUD5 | OTU domain containing 5 | 119 |
| 203859_s_at | PALM | Paralemmin | 117 |
| 244229_at | PARVG | parvin, gamma | 126 |
| 205656_at | PCDH17 | protocadherin 17 | 126 |
| 212390_at | PDE4DIP | phosphodiesterase 4D interacting protein | 120 |

S1

| Standard CDF probe set ID | genesymbol | Genename | number of leave-one-out iterations |
|---|---|---|---|
| 222860_s_at | PDGFD | platelet derived growth factor D | 123 |
| 216804_s_at | PDLIM5 | PDZ and LIM domain 5 | 116 |
| 212916_at | PHF8 | PHD finger protein 8 | 125 |
| 202846_s_at | PIGC | phosphatidylinositol glycan anchor biosynthesis, class C | 123 |
| 223733_s_at | PPP4R1L | protein phosphatase 4, regulatory subunit 1-like | 121 |
| 226065_at | PRICKLE1 | prickle homolog 1 (*Drosophila*) | 116 |
| 208257_x_at | PSG1 | pregnancy specific beta-1-glycoprotein 1 | 117 |
| 201198_s_at | PSMD1 | proteasome (prosome, macropain) 26S subunit, non-ATPase, 1 | 117 |
| 212187_x_at | PTGDS | prostaglandin D2 synthase 21 kDa (brain) | 119 |
| 212662_at | PVR | poliovirus receptor | 126 |
| 205326_at | RAMP3 | receptor (G protein-coupled) activity modifying protein 3 | 119 |
| 210568_s_at | RECQL | RecQ protein-like (DNA helicase Q1-like) | 123 |
| 1569294_at | RNF187 | ring finger protein 187 | 121 |
| 204632_at | RPS6KA4 | ribosomal protein S6 kinase, 90 kDa, polypeptide 4 | 123 |
| 225715_at | RPTOR | regulatory associated protein of MTOR, complex 1 | 123 |
| 234241_at | SCAMP5 | secretory carrier membrane protein 5 | 118 |
| 204035_at | SCG2 | secretogranin II (chromogranin C) | 117 |
| 224472_x_at | SDF4 | stromal cell derived factor 4 | 114 |
| 223121_s_at | SFRP2 | secreted frizzled-related protein 2 | 125 |
| 204051_at | SFRP4 | secreted frizzled-related protein 4 | 126 |
| 220973_s_at | SHARPIN | SHANK-associated RH domain interactor | 124 |
| 218765_at | SIDT2 | SID1 transmembrane family, member 2 | 119 |
| 209848_s_at | SILV | silver homolog (mouse) | 126 |
| 217507_at | SLC11A1 | solute carrier family 11 (proton-coupled divalent metal ion transporters), member 1 | 121 |
| 234948_at | SLC27A5 | solute carrier family 27 (fatty acid transporter), member 5 | 116 |
| 209897_s_at | SLIT2 | slit homolog 2 (*Drosophila*) | 115 |
| 203021_at | SLPI | secretory leukocyte peptidase inhibitor | 126 |
| 201073_s_at | SMARCC1 | SWI/SNF related, matrix associated, actin dependent regulator of chromatin | 120 |
| 209761_s_at | SP110 | SP110 nuclear body protein | 121 |
| 227737_at | SRPRB | signal recognition particle receptor, B subunit | 119 |
| 1570420_at | STXBP2 | syntaxin binding protein 2 | 117 |
| 203977_at | TAZ | tafazzin | 125 |
| 210144_at | TBC1D22A | TBC1 domain family, member 22A | 123 |
| 201813_s_at | TBC1D5 | TBC1 domain family, member 5 | 116 |
| 220417_s_at | THAP4 | THAP domain containing 4 | 126 |
| 227007_at | TMCO4 | transmembrane and coiled-coil domains 4 | 115 |
| 211282_x_at | TNFRSF25 | tumor necrosis factor receptor superfamily, member 25 | 126 |
| 203421_at | TP53I11 | tumor protein p53 inducible protein 11 | 126 |
| 212340_at | YIPF6 | Yip1 domain family, member 6 | 125 |
| 203043_at | ZBED1 | zinc finger, BED-type containing 1 | 121 |
| 232417_x_at | ZDHHC11 | zinc finger, DHHC-type containing 11 | 121 |
| 227902_at | ZFP41 | zinc finger protein 41 homolog (mouse) | 117 |
| 232408_at | ZFYVE28 | zinc finger, FYVE domain containing 28 | 115 |
| 1558942_at | ZNF765 | zinc finger protein 765 | 123 |

S2

| Custom CDF probe set ID | genesymbol | genename | number of leave-one-out iterations |
|---|---|---|---|
| 14_at | AAMP | angio-associated, migratory cell protein | 125 |
| 83858_at | ATAD3B | ATPase family, AAA domain containing 3B | 125 |
| 636_at | BICD1 | bicaudal D homolog 1 (*Drosophila*) | 116 |
| 11119_at | BTN3A1 | butyrophilin, subfamily 3, member A1 | 126 |
| 11118_at | BTN3A2 | butyrophilin, subfamily 3, member A2 | 126 |
| 81576_at | CCDC130 | coiled-coil domain containing 130 | 125 |
| 57124_at | CD248 | CD248 molecule, endosialin | 123 |
| 9249_at | DHRS3 | dehydrogenase/reductase (SDR family) member 3 | 123 |
| 64834_at | ELOVL1 | elongation of very long chain fatty acids (FEN1/Elo2, SUR4/Elo3, yeast)-like 1 | 114 |
| 2026_at | ENO2 | enolase 2 (gamma, neuronal) | 126 |
| 55793_at | FAM63A | family with sequence similarity 63, member A | 124 |
| 10468_at | FST | follistatin | 126 |
| 8325_at | FZD8 | frizzled homolog 8 (*Drosophila*) | 125 |
| 57120_at | GOPC | golgi-associated PDZ and coiled-coil motif containing | 118 |
| 8330_at | HIST1H2AK | histone cluster 1, H2ak | 120 |
| 3575_at | IL7R | interleukin 7 receptor | 117 |
| 3615_at | IMPDH2 | IMP (inosine monophosphate) dehydrogenase 2 | 118 |

S2

| Custom CDF probe set ID | genesymbol | genename | number of leave-one-out iterations |
|---|---|---|---|
| 2648_at | KAT2A | K(lysine) acetyltransferase 2A | 124 |
| 23383_at | KIAA0892 | KIAA0892 | 125 |
| 100289420_at | LOC100289420 | hypothetical protein LOC100289420 | 123 |
| 65258_at | MPPE1 | metallophosphoesterase 1 | 124 |
| 4485_at | MST1 | macrophage stimulating 1 (hepatocyte growth factor-like) | 126 |
| 389125_at | MUSTN1 | musculoskeletal, embryonic nuclear protein 1 | 116 |
| 10763_at | NES | nestin | 126 |
| 55193_at | PBRM1 | polybromo 1 | 117 |
| 27253_at | PCDH17 | protocadherin 17 | 125 |
| 5529_at | PPP2R5E | protein phosphatase 2, regulatory subunit B', epsilon isoform | 118 |
| 8986_at | RPS6KA4 | ribosomal protein S6 kinase, 90 kDa, polypeptide 4 | 117 |
| 7857_at | SCG2 | secretogranin II (chromogranin C) | 123 |
| 6423_at | SFRP2 | secreted frizzled-related protein 2 | 123 |
| 6424_at | SFRP4 | secreted frizzled-related protein 4 | 126 |
| 81858_at | SHARPIN | SHANK-associated RH domain interactor | 125 |
| 114789_at | SLC25A25 | solute carrier family 25 (mitochondrial carrier; phosphate carrier) | 119 |
| 9353_at | SLIT2 | slit homolog 2 (*Drosophila*) | 115 |
| 54471_at | SMCR7L | Smith-Magenis syndrome chromosome region, candidate 7-like | 126 |
| 6901_at | TAZ | tafazzin | 126 |
| 64222_at | TOR3A | torsin family 3, member A | 117 |
| 7278_at | TUBA3C | tubulin, alpha 3c | 122 |
| 5976_at | UPF1 | UPF1 regulator of nonsense transcripts homolog (yeast) | 124 |
| 10713_at | USP39 | ubiquitin specific peptidase 39 | 123 |
| 7586_at | ZKSCAN1 | zinc finger with KRAB and SCAN domains 1 | 120 |
| 84937_at | ZNRF1 | zinc and ring finger 1 | 118 |

S3

```
#Assigning expression risk score
#R version 2.13.0 (2011-04-13)
#Loading libraries
library(survival)
library(Biobase)
#Read the survival data - a tab-separated text file with censored survival data
survival_data <-read.table("survival_data.txt", sep="\t", header=TRUE, row.names=1)
print(survival_data[10:14,])
#         ISCHEMIC_time     ISCHEMIC_event
#286      1853              FALSE
#287      1852              FALSE
#288      643               TRUE
#289      1846              FALSE
#290      775               TRUE
#load BioC ExpressionSet containing RMA normalised expression data for plaque (bike_plaque hgu133plus2) and
PBMC (bike_cpt) data sets
load("Important R-images and cel files/bike expressionsets.rdata")
print(bike_plaque_hgu133plus2)
#ExpressionSet (storageMode: lockedEnvironment)
#assayData: 54675 features, 137 samples
#element names: exprs
#protocolData
#sampleNames: CG09_488P.CEL, CG10_491P.CEL, ..., P44_60.CEL (137 total)
#varLabels and varMetadata description:
#                    ScanDate: NA
#phenoData
#sampleNames: 488, 491, ..., 603 (137 total)
#varLabels and varMetadata description:
#                    General_Data_Age: NA
#General_Data_Gender: NA
#...: ...
#processing_cohort: NA
#(86 total)
#featureData: none
#experimentData: use 'experimentData(object)'
#Annotation: hgu133plus2
#iterate over the labels of interest
label<-"Ischemic"
#Iterate over the expressionsets analysed
expressionsetName<-"bike_plaque_hgu133plus2"
expressionsetName<-"bike_cpt"
#run on server
expressionset<-get(expressionsetName)
#adding survival data to the expressionset pData. Function found at end of document.
#Will add two columns to pdata - one with event censoring (TRUE/FALSE) and one with time (days).
expressionset <-fun_add_survival_data_to_pdata (expressionset , survival_data)
#remove the least expressed genes (the cutoff is arbitrary and conservative, but
#supported by expression levels of Y-chromosome genes in female samples)
expressionset<-fun_trim_min_expression (expressionset, cutoff = 1)
expressionset <-expressionset[featureNames(expressionset)[-grep(" AFFX",featureNames(expressionset))],]
#removing NA events and times and negative times
expressionset<-expressionset [,!is.na(expressionset [[paste(label,"_event",sep="")]])]
expressionset<-expressionset[,!is.na(expressionset[[paste(label,"_time",sep="")]])]
expressionset<-expressionset[,expressionset[[paste(label,"_time",sep="")]]>=0]
#creating a list of predictive probe sets in each iteration and iterating through
#all the samples to define which probe sets are predictive at 0.05
predictorProbesetsList<-list( )
for(leaveOutSample in sampleNames(expressionset)){
    trainExpressionset<-expressionset
    [,!sampleNames(expressionset)%in%leaveOutSample]
    survivalTime=trainExpressionset[[paste(label,"_time",sep="")]]
    survivalStatus=trainExpressionset[[paste(label,"_event",sep="")]]
    #Function to get cox-regression p-value
    getPredictivity<-function(expression, survivalStatus, survivalTime){
        summary(coxph( Surv(survivalTime,survivalStatus) ~ expression, na.action=na.omit)
```

```
S3

))[["coefficients"]]["expression",c("coef","Pr(>|z|)
        ")]
    }
    #application of this function to all genes
    predictivity<-t(apply(exprs(trainExpressionset),1,getPredi
    ctivity,survivalStatus,survivalTime))
    predictivity<-predictivity[order(predictivity[, "Pr (>|z|)"]
    ),]
    #saving the significant probe sets in the
    predictorProbesetsList
    predictorProbesets<-rownames(predictivity)[predictivity[,"
    Pr(>|z|)"]<0.05]
    predictorProbesetsList[[leaveOutSample]]<-predictivity
    [predictorProbesets,]
}
#creating a vector for the cross-validated expression risk score
leaveOutSampleRisks<-vector( )
for(leaveOutSample in sampleNames(expressionset)){
        predictivity<-predictorProbesetsList[[leaveOutSample]]
        predictorProbesets<-rownames(predictivity)[predictivity[,"
        Pr(>|z|)"] < 0.05]
        if(length(predictorProbesets)<2)stop("no predictor probe
        sets")
        meanValues<-apply(
            exprs(expressionset[,!sampleNames(expressionset)%in%
            leaveOutSample])
            [predictorProbesets,],1,mean)
        leaveOutSamplePredictorDifference<-exprs(expressionset)[pr
        edictorProbesets,leaveOutSample] - meanValues
        leaveOutSampleRisk <-sum(leaveOutSamplePredictorDifference
        * -
        predictivity[predictorProbesets,"coef"])
        leaveOutSampleRisks<-c(leaveOutSampleRisks,leaveOutSampleR
        isk)
}
names(leaveOutSampleRisks)<-sampleNames(expressionset)
save(leaveOutSampleRisks,predictorProbesetsList,file="leaveOutSample
Risks.rdata")
#Define function that can add survival data to expressionsets
fun_add_survival_data_to_pdata<-function (expressionset,
survival_data){
    library(Biobase)
    if (class(expressionset)[1] != "ExpressionSet")
        stop("expressionset argument must be an ExpressionSet")
    if (class(survival_data) != "data.frame")
        stop("survival_data argument must be a data.frame")
    for (label in colnames(survival_data)) {
        if (!(length(grep("_event$", label)) == 1 |
        length(grep("_time$",label)) == 1)) {
        stop(paste(label, "must end with either _time or _event"))
|
            if (label %in% colnames(pData(expressionset))) {
                stop(paste(label, "was already found in
                expressionset"))
            }
        }
    }
    if ("survival_data_labels" %in% names(notes(expressionset)))
        stop("survival_data_labels has already been added to this
        expressionset. Probably better to start over")
    if (sum(rownames(survival_data) %in% sampleNames(expressionset))
    == 0)
        stop("Didn't find any of the rownames of survival_data as
        sampleNames in expressionset")
    if(sum(sampleNames(expressionset) %in% rownames(survival_data))
    == 0)
        stop("Didn't find any of the rownames of survival_data as
        sampleNames in expressionset")
    labels -colnames(survival_data)
    labels <-sub("_event", "", labels)
    labels <-sub("_time", "", labels)
    labels <-unique(labels)
    print(paste("Adding survival data to", length(intersect
    (sampleNames(expressionset),
    rownames(survival_data))), "samples of the",
    ncol(expressionset), "in",
    expressionset@experimentData@title, "for the", length(labels),
```

```
S3

"labels found in survival_data:",
    paste(labels, collapse = ", ")))
    pData(expressionset) <-cbind(pData(expressionset),
    survival_data[sampleNames(expressionset),])
    notes(expressionset)[["survival_data_labels"]] <-labels
    return(expressionset)
}
#Define function used for filtering data on minimum expression
levels set relative to all expression levels
fun_trim_min_expression<-function (expressionset, verbose = TRUE,
cutoff = 1){
    sample_before_trimming <-nrow(expressionset)
    cutoff_value <-mean(exprs(expressionset)) * cutoff
    sorting_vector <-apply(exprs(expressionset), 1, mean) >
    cutoff_value
    expressionset <-expressionset[sorting_vector, ]
    sample_after_trimming <-nrow(expressionset)
    if (verbose) {
        print(paste("expressionset trimming:",
        sample_before_trimming - sample_after_trimming, "probe
        sets out of", sample_before_trimming, "were removed
        because their mean was below", cutoff, "times the mean
        of the entire set"))
    }
    return(expressionset)
}
```

We claim:

1. A method of profiling endarterectomy patients for determining one or more post-operative risks, characterized in that said method includes:
    (a) obtaining a set of parameters which describe the patient, said set of parameters including at least one of: age of patient, E; smoking habits of patient, S; serum cholesterol concentration of patient, C; diabetes status of patient, D; blood pressure of patient, P;
    (b) obtaining one or more samples of plaque tissue from endarterectomy treatment of said patient;
    (c) isolating mRNA from said one or more samples of plaque tissue;
    (d) determining genetic expression activities of a plurality of genes identified in said genetic material; and
    (e) computing from said set of parameters in combination with said genetic expression activities one or more post-operative risks indicative of potential events to which the patient is susceptible as a consequence of said endarterectomy treatment; and
    in step (e), a blinded cross-validation iterative computation is performed for computing said one or more risks.

2. A method as claimed in claim 1, wherein said isolated mRNA corresponds to a total RNA content of said one or more samples of plaque tissue.

3. A method as claimed in claim 1, wherein said profiling endarterectomy is performed for carotid enartecectomy, and wherein step (b) when obtaining one or more samples of plaque tissue it is from carotid endarterectomy treatment of said patient.

4. A method as claimed in claim 1, wherein a step (e) includes excluding from computation of the one or more risks gene expressions which lie below a threshold expression limit.

5. A method as claimed in claim 1, wherein said threshold expression limit is determined from an average expression exhibited by a plurality of genes obtained from said one or more samples of plaque tissue.

6. A method as claimed in claim 1, wherein said method includes excluding from computation of the one or more risks RNA material whose RNA purity is less than a purity threshold limit.

7. A method as claimed in claim 1, wherein said plurality of genes are derived from cytoplasm, plasma membranes and mitochondria included in said one or more samples of plaque tissue.

8. A method as claimed in claim 1, wherein the mRNA includes a set of genes, wherein substantially 13.2% of the genes are localized to cytoplasm.

9. A method of profiling endarterectomy patients for determining one or more post-operative risks, characterized in that said method includes:
   (a) obtaining a set of parameters which describe the patient, said set of parameters including at least one of: age of patient, E; smoking habits of patient, S; serum cholesterol concentration of patient, C; diabetes status of patient, D; blood pressure of patient, P;
   (b) obtaining one or more samples of plaque tissue from endarterectomy treatment of said patient;
   (c) isolating mRNA from said one or more samples of plaque tissue;
   (d) determining genetic expression activities of a plurality of genes identified in said genetic material; and
   (e) computing from said set of parameters in combination with said genetic expression activities one or more post-operative risks indicative of potential events to which the patient is susceptible as a consequence of said endarterectomy treatment; and
   wherein in step (e) of the method involves computing Cox regression coefficients for assigning a gene expression-based risk score to said patient.

10. A method as claimed in claim 1, including an additional step of designing a post-treatment care strategy based upon said computed one or more post-operative risks indicative of potential events.

11. A method according to claim 9, wherein in step (e) of the method additionally comprises a blinded cross-validation iterative computation for computing said one or more risks.

12. A method according to claim 1, wherein step (e) of the method additionally comprises computing Cox regression coefficients for assigning a gene expression-based risk score to said patient.

13. A method as claimed in claim 9, wherein said isolated mRNA corresponds to a total RNA content of said one or more samples of plaque tissue.

14. A method as claimed in claim 9, wherein said profiling endarterectomy is performed for carotid enartecectomy, and wherein step (b) when obtaining one or more samples of plaque tissue it is from carotid endarterectomy treatment of said patient.

15. A method as claimed in claim 9, wherein a step (e) includes excluding from computation of the one or more risks gene expressions which lie below a threshold expression limit.

16. A method as claimed in claim 9, wherein said plurality of genes are derived from cytoplasm, plasma membranes and mitochondria included in said one or more samples of plaque tissue.

17. A method as claimed in claim 9, wherein the mRNA includes a set of genes, wherein substantially 13.2% of the genes are localized to cytoplasm.

18. A method as claimed in claim 9, wherein said threshold expression limit is determined from an average expression exhibited by a plurality of genes obtained from said one or more samples of plaque tissue.

19. A method as claimed in claim 9, wherein said method includes excluding from computation of the one or more risks RNA material whose RNA purity is less than a purity threshold limit.

20. A method as claimed in claim 9, including an additional step of designing a post-treatment care strategy based upon said computed one or more post-operative risks indicative of potential events.

* * * * *